United States Patent [19]

Benner

[11] Patent Number: 6,001,983
[45] Date of Patent: *Dec. 14, 1999

[54] OLIGONUCLEOTIDES WITH NON-STANDARD BASES AND METHODS FOR PREPARING SAME

[76] Inventor: Steven Albert Benner, 1501 NW. 68th Ter., Gainesville, Fla. 32605-4147

[*] Notice: This patent is subject to a terminal disclaimer.

[21] Appl. No.: 08/375,132

[22] Filed: Jan. 17, 1995

Related U.S. Application Data

[63] Continuation-in-part of application No. 07/594,290, Oct. 9, 1990, Pat. No. 5,432,272.
[51] Int. Cl.$^6$ .............................. C07H 1/00; C07H 21/00
[52] U.S. Cl. .................... 536/23.1; 536/25.3; 536/25.31; 536/25.32; 536/25.33; 536/25.34; 536/25.4; 435/91.1; 435/91.41
[58] Field of Search .................................. 536/23.1, 25.3, 536/28.1, 27.21, 25.31, 25.32, 25.33, 25.34, 25.4, 22.1; 435/91.1, 91.41

[56] References Cited

U.S. PATENT DOCUMENTS

| | | | |
|---|---|---|---|
| 5,126,439 | 6/1992 | Rappaport | 536/23.1 |
| 5,432,272 | 7/1995 | Benner | 536/25.3 |

OTHER PUBLICATIONS

Golas, T., et al., Preparation and Properties of an Analogue of Poly(A) and Poly(G): Poly(isoguanylic acid), J. Biochem, 65:183–192, (1976).

*Primary Examiner*—James O. Wilson

[57] ABSTRACT

The disclosure describes new compositions of matter that are analogs of DNA and RNA containing heterocyclic bases that can form base pairs that fit the Watson-Crick geometry in that they involve a monocyclic six membered ring pairing with a fused bicyclic heterocyclic ring system composed of a five member ring fused with a six membered ring, with the orientation of the heterocycles with respect to each other and with respect to the backbone chain analogous to that found in DNA and RNA, but where these base pairs are joined by a pattern of hydrogen bonds different from that found in the AT and GC base pairs (a "non-standard base pair").

6 Claims, 9 Drawing Sheets

Fig. 5

Templates for T7 RNA polymerase d-5'-GATTTTGA
d-3'-CTAAAACTGGKGA d-5'-GATTTTGA
d-3'-CTAAAACTGG*iso*-CGA d-5'-GATTTTGA
d-3'-CTAAAACTGGTGA d-5'-GATTTTGA
d-3'-CTAAAACTGGCGA Templates for DNA polymerase d-5'-TAATACGACTCACTATAG
d-3'-ATTATGCTGAGTGATATCGCGGCKCGA d-5'-TAATACGACTCACTATAG
d-3'-ATTATGCTGAGTGATATCGCGGC*iso*-CCGA d-5'-TAATACGACTCACTATAG
d-3'-ATTATGCTGAGTGATATCGCGGCCCGA ated optimization by non-linear analysis. *J. Mol Biol*

OLIGONUCLEOTIDES WITH NON-STANDARD BASES AND METHODS FOR PREPARING SAME

This is a continuation in part of the patent application Ser. No. 07/594,290, filed: Oct. 09, 1990 now U.S. Pat. No. 5,432,272. Ser. No. 07/594,290 now U.S. Pat. No. 5,432,272 discloses a method for synthesizing oligonucleotide analogs using DNA and RNA polymerases to incorporate nucleotides (non-standard nucleotides) capable of forming non-standard Watson-Crick base pairs joined by patterns of hydrogen bonding different from those found in the adenine-thymine and cytosine-guanine base pairs. The claims in U.S. Pat. No. 5,432,272 refer to methods of incorporating non-standard nucleotides into DNA and RNA. The claims in the instant continuation cover compositions of matter that are oligonucleotide analogs resulting from application of the methods claimed in U.S. Pat. No. 5,432,272.

BACKGROUND OF THE INVENTION

1. Field of the Invention

These compositions of matter have multiple uses, including as components of libraries that are the starting point for in vitro selection experiments. Therefore, this invention also relates to methods for preparing ligands that bind tightly to a preselected biological receptor using a process of in vitro selection. More particularly, the present invention pertains to compositions and methods for generating libraries of oligonucleotide analogs built from a combination of natural nucleotides, natural nucleotides bearing functionalized side chains, and at least one nucleotide building unit with a non-standard hydrogen bonding pattern, either bearing or not bearing a functionalized side chains. The library can be enriched in those oligonucleotide analog sequences that have an affinity for the preselected biological receptor, these sequences can be amplified by those oligonucleotide analog sequences that are bound to the receptor using DNA and RNA polymerases by the methods already covered by claims in U.S. Pat. No. 5,432,272, mutating the amplified products, and repeating the cycle of enrichment, amplification, and mutation to obtain libraries of oligonucleotides with improved affinity for the preselected receptor. Also, the method of this invention may be applied to the generation of oligonucleotide analogs with catalytic activity against a preselected substrate.

2. Description of the Related Art

Background

The majority of pharmaceutical agents are compounds that exert their biological activity by binding to a biological macromolecule, referred to here as a receptor. The discovery of ligands that can bind to a preselected receptor and thereby exert a biological effect is an important goal of medicinal chemists seeking to develop new human pharmaceutical agents.

Classically, ligands are discovered by three strategies. The first involves screening of a collection of chemicals whose structures have no deliberate connection with the structure or biology of the target receptor. This process is referred to as "random screening".

The second strategy requires information about the structure of the natural ligand for a receptor. Development of new ligands then is based on the deliberate synthesis of specific analogs of the natural ligand in the hope of discovering a ligand that retains or has increased affinity for the receptor, together with bioavailability, stability, and other properties desired for a human pharmaceutical.

The third strategy requires information about the structure of the receptor itself. With this information, ligands are designed by the design of structures that are complementary to the binding site of the ligand.

The deficiencies of these three approaches are well known to those familiar with the art. Random input screening often requires examination of thousands of compounds before a single ligand has a chance of being identified. Analogs of the natural ligands often resemble the natural ligand in terms of bioavailability, stability, or other properties; often, these properties are undesirable in a human pharmaceutical. Further, while tremendous strides have been made in the science of molecular recognition over the past decade, it is still not possible to design a ligand for a receptor even given a high resolution experimental structure for the receptor itself.

One approach suggested for approaching these problems comes under the title of "in vitro selection". The approach has several implementations. In each, a collection, or library, of oligonucleotides of random sequence is presented to the receptor attached to a solid support. The receptor binds to only a few oligonucleotides in the library. The oligonucleotides in the pool that do not bind to the receptor are first washed from the support. The oligonucleotides that bind to the receptor tightly are then eluted from the receptor and recovered. These are then amplified by polymerase chain reaction technology, well known in the art, to yield a library of oligonucleotides whose members have a higher affinity, on average, than the members of the original pool. This new library is then subjected to mutation by methods well known in the art to create a new library of oligonucleotides with structures randomized around those of the starting library with increased affinity for the receptor. These are then subjected to the binding, elution, and amplification steps in repeated cycles, leading to oligonucleotides with increased binding activity. When selection methods permit enrichment of oligonucleotides with a particular catalytic activity, catalysis can also be selected by this process.

The elements of this approach are reviewed in the following publications.

Irvine, D., Tuerk, C., Gold, L. (1991) Selexion. Systematic evolution of ligands by exponential enrichment with integrated optimization by non-linear analysis. *J. Mol Biol* 222, 739–761.

Szostak, J. W. (1992) In vitro genetics. Trends Biochem. Soc. 17, 89–93.

An example of the use of this approach to obtain oligonucleotides as ligands for reverse transcriptase is reported in the following publication: Chen, H., Gold, L. (1994) Selection of high affinity RNA ligands to reverse transcriptase. *Biochemistry* 33, 8746–8756.

The primary difficulty in this approach arises from the fact that natural oligonucleotides are built from only four building blocks. Further, these building blocks carry relatively little interesting functionality, especially compared to that carried by proteins. Thus, oligonucleotides with tight affinity for some receptors occur only infrequently in a population of random oligonucleotides, in some cases no oligonucleotides can be found that bind effectively to some receptors, the catalytic effectiveness of oligonucleotides selected to be catalysts is limited, and there is a limit to which an oligonucleotide of a defined size can bind to a receptor. This makes it difficult to identify oligonucleotides within a library of standard oligonucleotide sequences that have satisfactory binding or catalytic properties.

The approach of the instant invention to circumvent limitations of in vitro selection systems that start from libraries of oligonucleotides built fully from standard nucleotides (ribo or deoxyribo adenylic acid, guanylic acids, cytidylic acid, and uridylic acid or thymidylic acid, incorporated in an oligonucleotide, referred to in context by convention as A, G, C, T and U) can be better understood by first understanding the mechanism by which complementary oligonucleotides recognize each other, and how complementarity is used in polymerase chain reaction amplification of oligonucleotides during an in vitro selection cycle. Natural oligonucleotides bind to complementary oligonucleotides according to the well-known rules of base pairing first elaborated by Watson and Crick, where adenine (A) pairs with thymine (T) or uracil (U), and guanine (G) pairs with cytosine (C), with the complementary strands anti-parallel to one another. These pairing rules allow for the specific hybridization of an oligonucleotide with complementary oligonucleotides, making oligonucleotides valuable as probes in the laboratory, in diagnostic applications, as messages that can direct the synthesis of specific proteins, and in a wide range of other applications well known in the art. Further, the pairing is the basis by which enzymes are able to catalyze the synthesis of new oligonucleotides that are complementary to template nucleotides. In this synthesis, building blocks (normally the triphosphates of ribo or deoxyribo derivatives of A, T, U, C, or G) are directed by a template oligonucleotide to form a complementary oligonucleotide with the correct sequence. This process is the bases for replication of all forms of life, and also serves as the basis for all technologies for enzymatic synthesis and amplification of specific heterosequence nucleic acids by enzymes such as DNA and RNA polymerase, and in the polymerase chain reaction.

The Watson-Crick pairing rules can be understood chemically in terms of the arrangement of hydrogen bonding groups on the heterocyclic bases of the oligonucleotide, groups that can either be hydrogen bond donors or acceptors (FIG. 1). In the standard Watson-Crick geometry, a large purine base pairs with a small pyrimidine base; thus, the AT base pair is the same size as a GC base pair. This means that the rungs of the DNA ladder, formed from either AT or GC base pairs, all have the same length.

Further recognition between bases is determined by hydrogen bonds between the bases. Hydrogen bond donors are heteroatoms (nitrogen or oxygen in the natural bases) bearing a hydrogen; hydrogen bond acceptors are heteroatoms (nitrogen or oxygen in the natural bases) with a lone pair of electrons. In the geometry of the Watson-Crick base pair, a six membered ring (in natural oligonucleotides, a pyrimidine) is juxtaposed to a ring system composed of a fused six membered ring and a five membered ring (in natural oligonucleotides, a purine), with a middle hydrogen bond linking two ring atoms, and hydrogen bonds on either side joining functional groups appended to each of the rings, with donor groups paired with acceptor groups (FIG. 1).

Derivatized oligonucleotide building blocks, where a side chain has been appended to one of the nucleoside bases A, T, U, G, or C (the "normal" bases), have application because of their combination of Watson-Crick base pairing and special reactivity associated with the chemical properties of the side chain. For example, oligonucleotides containing a T to which is appended a side chain bearing a biotin residue can first bind to a complementary oligonucleotide, and the hybrid can then be isolated by virtue of the specific affinity of biotin to avidin (Langer, P. R.; Waldrop, A. A.; Ward, D. C. (1981) *Proc. Nat. Acad. Sci.* 78, 6633–6637), and finds application in diagnostic work. Oligonucleotides containing special functional groups (e.g., thiols or hydrazines) can be immobilized to solid supports more readily than those composed solely of the five "natural" bases.

Often, derivatized building blocks can be incorporated into oligonucleotides by enzymatic transcription of natural oligonucleotide templates in the presence of the triphosphate of the derivatized nucleoside, the substrate of the appropriate (DNA or RNA) polymerase. In this process, a natural nucleoside is placed in the template, and standard Watson-Crick base pairing is exploited to direct the incoming modified nucleoside opposite to it in the growing oligonucleotide chain.

However, the presently available base pairs are limited in that there are only two mutually exclusive hydrogen bonding patterns available in natural DNA. This means that should one wish to introduce a modified nucleoside based on one of the natural nucleosides into an oligonucleotide, it would be incorporated wherever the complementary natural nucleoside is found in the template. For many applications, this is undesirable.

SUMMARY OF THE INVENTION

U.S. Pat. No. 5,432,272 has disclosed methods for synthesizing oligonucleotide analogs built from nucleosides carrying nucleobases that can form base pairs using non-standard hydrogen bonding patterns. By using non-standard hydrogen bonding patterns, the number of independently replicating building blocks in an oligonucleotide can be increased from four to six, eight or more, to a maximum of twelve. The objective of this cited invention was to increase the number of independently replicatable building blocks that can be incorporated into DNA and RNA via template directed polymerization. The objective is accomplished by a method for incorporating into double stranded DNA and RNA base pairs composed of pairing units that fit the Watson-Crick geometry in that they involve a monocyclic six membered ring pairing with a fused bicyclic heterocyclic ring system composed of a five member ring fused with a six membered ring, with the orientation of the heterocycles with respect to each other and with respect to the backbone chain analogous to that found in DNA and RNA, but with a pattern of hydrogen bonds holding the base pair together different from that found in the AT and GC base pairs (a "non-standard base pair"). The claims of the instant application cover compositions of matter made using the methods of U.S. Pat. No. 5,432,272, and the use of these compositions as components of a library as the starting point for in vitro selection experiments.

BRIEF DESCRIPTION OF THE DRAWINGS

FIG. 5: Templates used in the examples

DETAILED DESCRIPTION OF THE INVENTION AND PREFERRED EMBODIMENTS

Summary of the Invention

This invention is based on the fact that novel bases with patterns of hydrogen bond donors and acceptors that are different from those found in the normal A-T (or A-U) and G-C base pairs ("non-standard" hydrogen bonding patterns) can fit the standard Watson-Crick geometry. Thus, in the naturally-occurring Watson-Crick base pairs, the pyrimidines components present an acceptor-donor-acceptor (T) or a donor-acceptor-acceptor (C) pattern of hydrogen bonds to purines on an opposite strand presenting a donor-acceptor-donor (aminoadenine) or acceptor-donor-donor (G) hydrogen bonding pattern. To systematize the nomenclature in this disclosure. Pyrimidines are designated by the prefix "pu", purines by the prefix "pu". Following the prefix is the order, from the major groove to the minor groove, of acceptor (A) and donor (D) groups. By this systematic nomenclature, thymine is designated py(ADA), cytosine is designated py(DAA), and gunanine is designated pu(ADD). Note that in natural nucleosides, adenosine (pu(DA-)) incompletely implements the Watson-Crick hydrogen bonding strategy; the purine fully complementary to T or U is 2,6-diaminopurine or any of its analogs that presents a pu(DAD) hydrogen bonding pattern to a complementary strand.

Figure 1:
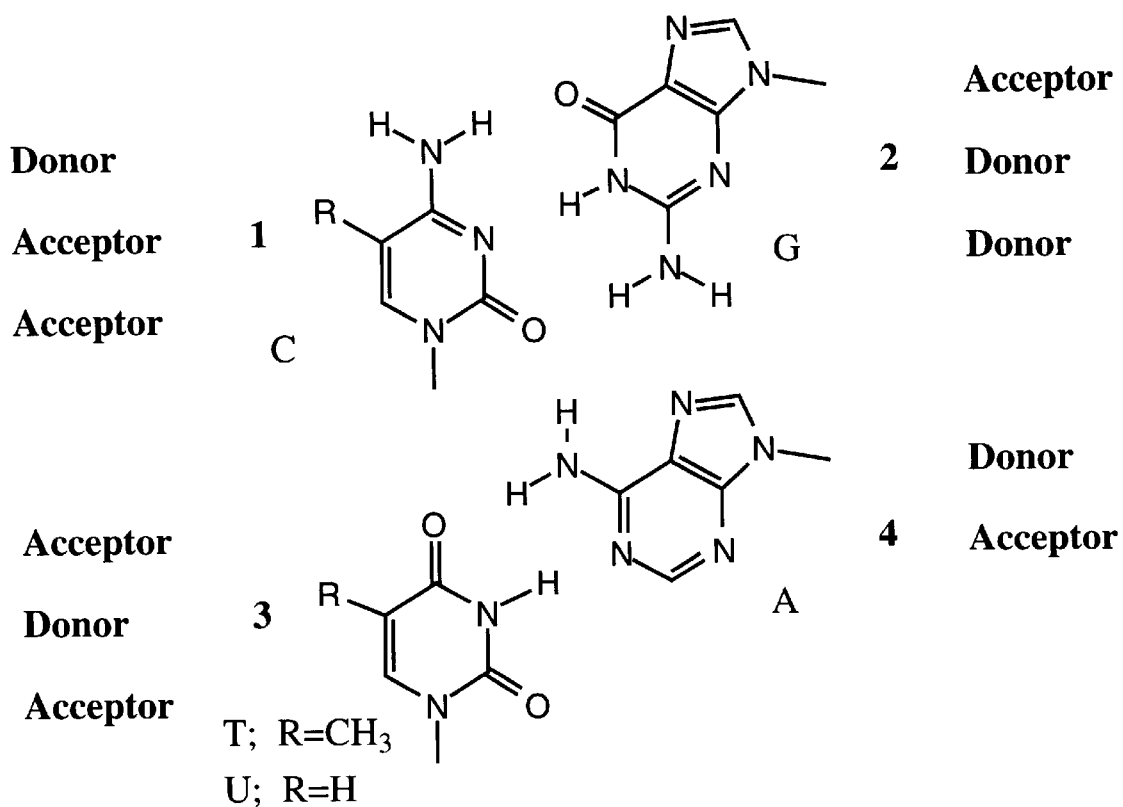
FIG. 1: The two natural base pairs formed between the four natural bases

However, other patterns are possible. For example, FIG. 1 discloses four base pairs that have still different patterns, an acceptor-acceptor-donor pattern for iso-C (py(AAD)), and donor-acceptor-donor pattern for κ(py(DAD)). Bases, pairing schemes, and base pairs that have hydrogen bonding patterns different from those found in the AT and GC base pairs are here termed "non-standard". Although not found (to our knowledge) in Nature, the non-standard base pairs shown in FIG. 2) apparently can fit into the DNA ladder in a standard Watson-Crick duplex.

Figure 2:
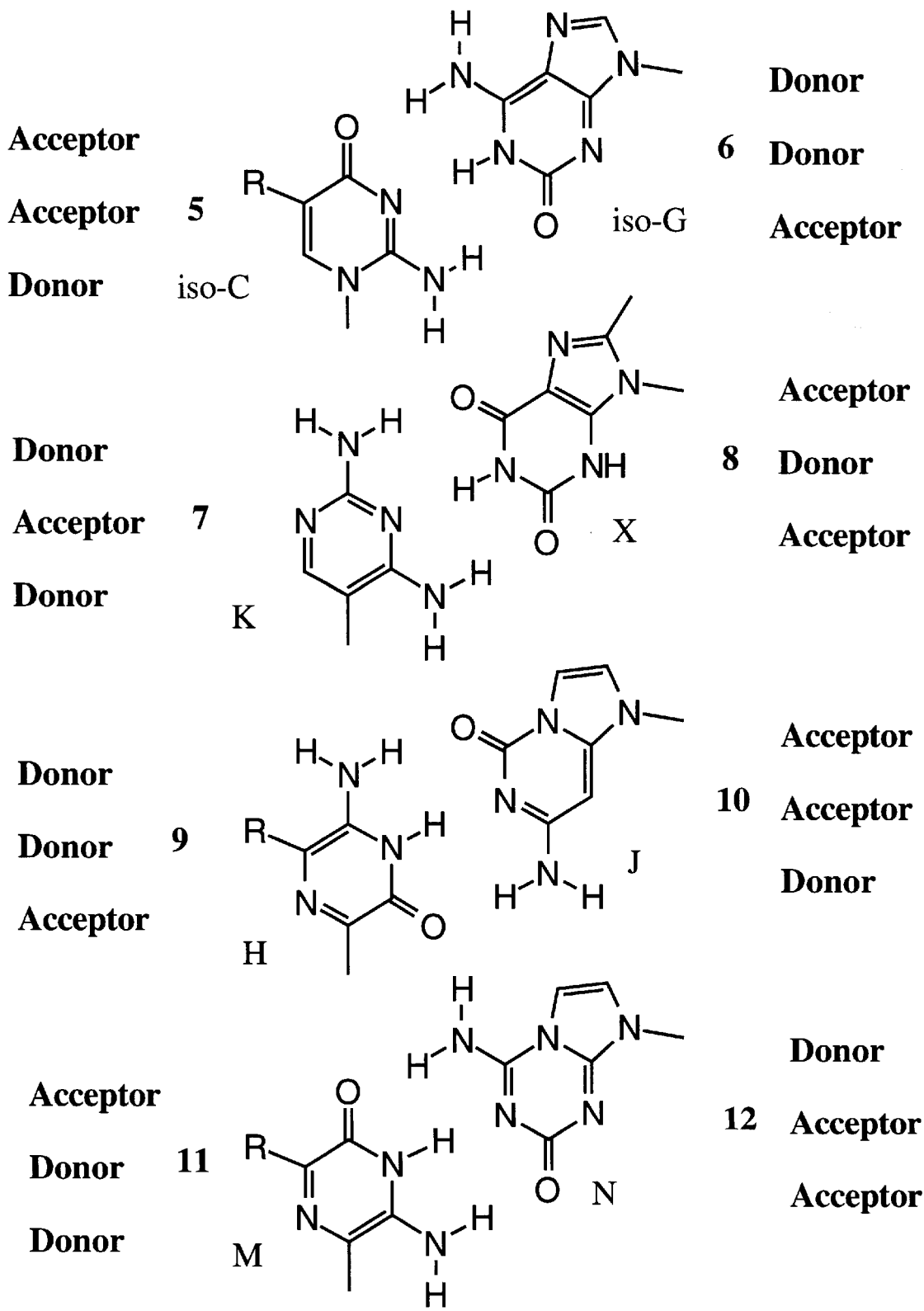
FIG. 2: Examples of 4 non-standard base pairs formed between 8 non-standard bases

Further, the patterns of hydrogen bonds in these non-standard pyrimidines are different from each other, and different from those in the natural pyrimidines T and C. This suggested that in an enzyme-catalyzed polymerization, it might be possible for each non-standard pyrimidine to recognize uniquely its complementary purine with high fidelity. Thus, it should be possible to make copies of a DNA molecule containing all 12 bases simply by following an expanded set of Watson-Crick rules: A pairs with T, G pairs with C, iso-C pairs with iso-G, and K pairs with X, H pairs with J, and M pairs with N (FIG. 2). In other words, it should be possible to have a genetic alphabet with twelve bases instead of four.

Statements considering non-standard base pairs in a general way can, to our knowledge, be found only three times previously in the literature. Considering possible bases that might have been incorporated into nucleic acids in the first forms of life on the earth two to four billion years ago, Rich mentions the base pair between iso-G and iso-C (Rich, A. (1962), Horizons in Biochemistry, Kasha, M. and Pullman, B. editors, NY., Academic Press, 103–126)as a base pair that was conceivable, but rejected, by the earliest forms of life. However, Rich did not disclose nor make obvious the process disclosed here employing contemporary DNA and RNA polymerases as part of a process for incorporating the base pair between iso-G and iso-C into oligonucleotides, nor prepared any compositions containing iso-C and iso-G. Saenger (Saenger, W. (1985) Nucleic Acid Chemistry, Springer-Verlag) also mentions this base pair, but concludes, based on the fact that iso-G has a alternate tautomeric forms (vide infra), that it has no utility as part of an oligonucleotide that is to be copied.

Figure 3:
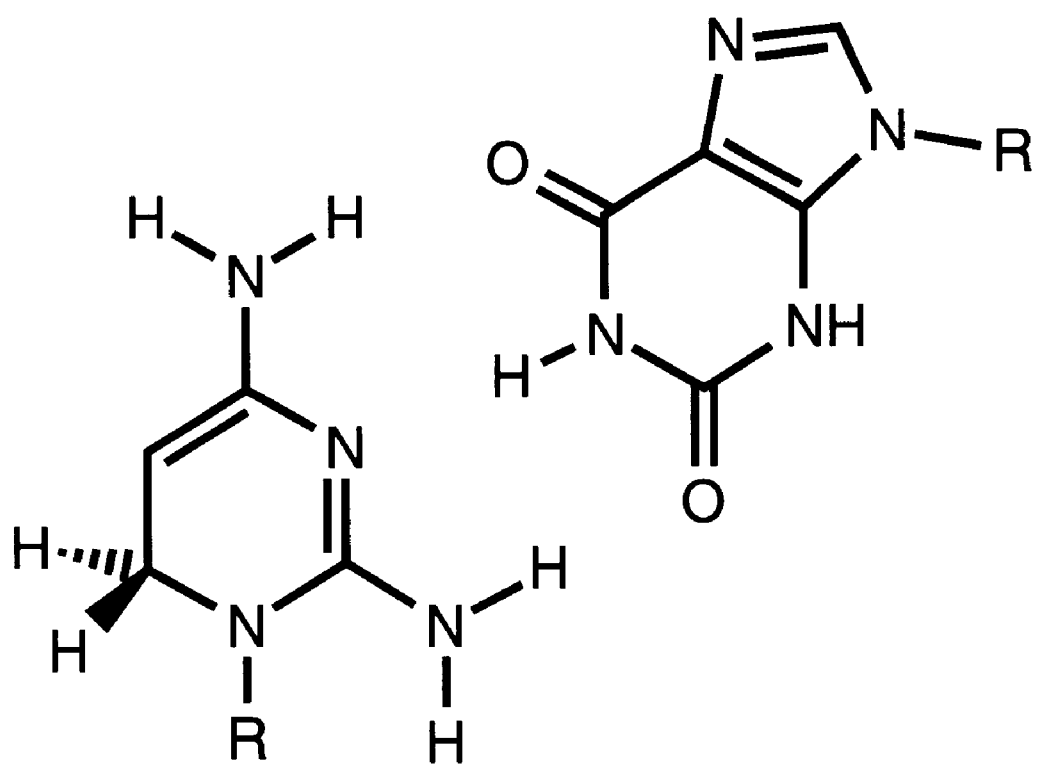
FIG. 3: Novel base pair discussed by Zubay

Zubay (Zubay, G. (1988) The Roots of Modern Biochemistry, Kleinkauf, von Doehren, Jaenicke, Berlin, Walter de Gruyter & Co. 911–916) suggested that 2,4-diamino-5,6-dihydropyryimidine-1-riboside, with a donor-acceptor-donor pattern, might be able to pair with xanthosine (FIG. 3). In Zubay's suggested pyrimidine, however, the pyrimidine ring is not aromatic and therefore not planar. Although it has never been examined experimentally, we believe on these grounds that it would not participate well in "base stacking," the interaction (vide supra) that is important for the stability of a double helix. Further, Zubay's base incorporates the structural unit known as a "vinylogous enamine", a structural unit that is likely to be unstable in acidic solution. Thus, we doubt that it can be incorporated into an oligonucleotide by enzymatic transcription of a complementary oligonucleotide.

Zubay discloses neither experimental studies with his suggested base nor the potential utility of a new base pair that would arise were the new base a substrate for DNA and RNA polymerases present in the modern world. Further, the possibility of constructing additional base pairing schemes (such as the non-standard base pairs disclosed in FIG. 2) was explicitly denied. Zubay writes "We have searched for other purine-pyrimidine base pairs with different arrangements of hydrogen bonding groups that would satisfy the criterion of exclusive pairing. No additional pairs have been found. Thus except for modifications at non-hydrogen bonding sites the additional base pair described here may be unique." This comment from a prominent figure in American biochemistry supports the notion that the invention disclosed here, where DNA and RNA polymerases can be used in a method to incorporate non-standard base pairs into oligonucleotides, is not obvious to one skilled in the art.

Should the additional base pairs disclosed in FIG. 2 be incorporated enzymatically into DNA and RNA, they could be useful for a variety of purposes. For example, RNA molecules prepared by transcription, although it is known to be a catalyst under special circumstances ((a) Cech, T. R.; Bass, B. L. Ann. Rev. Biochem. 1986, 55, 599. (b) Szostak, J. W. Nature 1986, 332, 83. (c) Been, M. D.; Cech, T. R. Science 1988, 239, 1412), appear to have a much smaller catalytic potential than proteins because they lack building blocks bearing functional groups. Conversely, the limited functionality present on natural oligonucleotides constrains the chemist attempting to design catalytically active RNA molecules, in particular, RNA molecules that catalyze the template-directed polymerization of RNA.

Additional base pairs could relax these constraints, especially if their hydrogen bonding pattern differed from those in the AT and GC base pairs, as novel hydrogen bonding schemes would allow additional base pairs to be incorporated enzymatically at specific positions in an oligonucleotide molecule (Switzer, C. Y, Moroney, S. E. & Benner, S. A. J. Am. Chem. Soc., 1989, 111, 8322). If functionalized, such additional bases should also allow the incorporation by transcription of functional groups directly into RNA; the remaining unfunctionalized building blocks could then control secondary structure without introducing overfunctionalization and attendant non-specific catalysis. Further, bases bearing functional groups at the position structurally analogous to the 5-position of the uridine ring should be substrates for most polymerases (Leary, J. L., Brigati, D. J. & Ward, D. C. Proc. Natl. Acad. Sci. 1983, 80, 4045). New base pairs should also find use in studies of the structure of biologically important RNA and DNA molecules (Chen, T. R., Churchill, M. E. A., Tullius, T. D. Kallenbach, N. R., Seemann, N. C. (1988) *Biochem.,* 27, 6032) and protein-nucleic acid interactions. Several types of catalytic RNA molecules containing natural bases have been proposed as anti-viral agents, for use in agriculture, and in other areas. (Haseloff, J., Gerlach, W. L. *Nature,* 1988, 334, 585; Sarver, N., Cantin, E. M., Chang, P. S., Zaia, J. A., Ladne, P. A., Stephens, D. A., Rossi, J. J. *Science,* 1990, 247, 1222–1225). Catalytic RNA molecules incorporating additional bases should be even more useful in certain of these applications. A segment of DNA or RNA containing the additional bases could be replicated only in the presence of triphosphates of the complementary additional bases, allowing the selective copying of DNA containing the additional bases in the presence of DNA containing normal bases, and vice versa. More speculatively, the extra letters in the nucleoside alphabet might eventually be used to expand the genetic code, increasing the number of amino acids that can be incorporated translationally into proteins Noren, C. J., Anthony-Cahili, S. J., Griffith, M. C. & Schultz, P. G. *Science,* 1989, 244, 182; J. D. Bain, J C. G. Glabe, T. A. Dix, A. R. Chamberlain *J. Am. Chem. Soc.* 1989, 111, 8013–8014.

We describe here a process for incorporating bases with special hydrogen bonding schemes into an oligonucleotide (DNA or RNA) chain that comprises the synthesis of an oligonucleotide template containing one or more additional bases, and incubating the template with either a DNA or RNA polymerase (Uhlenbeck, O. C. *Nature,* 1987, 328, 18) in the presence of triphosphates of the complementary nucleosides.

Description of the Preferred Embodiments

Experiments with iso-C (py(AAD)) and iso-G (pu(DDA)) (FIG. 2) have shown that bases with novel hydrogen bonding schemes can be incorporated by DNA and RNA polymerases to yield compositions of matter containing these non-standard bases. Thus, this base pair fulfills the criteria outlined above. However, certain forms of iso-C were found to hydrolyze slowly to U under conditions of DNA synthesis, introducing into a template a base that pairs with A in the place of a base that pairs with iso-G. Further, iso-G exists to some extent in a minor tautomeric form that is complementary to U and T. Although the existence of a minor tautomeric form of iso-G has some advantages in certain circumstances (e.g., when one wishes to introduce iso-G into an oligonucleotide duplex opposite U or T), these problems complicate the selective incorporation of the iso-C/iso-G base pair in oligonucleotides also containing A and T. Therefore, the search for a preferred embodiment was directed towards base pairs in FIG. 2 where the non-standard base is joined to the sugar by a carbon-carbon bond, where chemical considerations suggested that hydrolysis and tautomeric equilibria might be less problematic.

Figure 4:
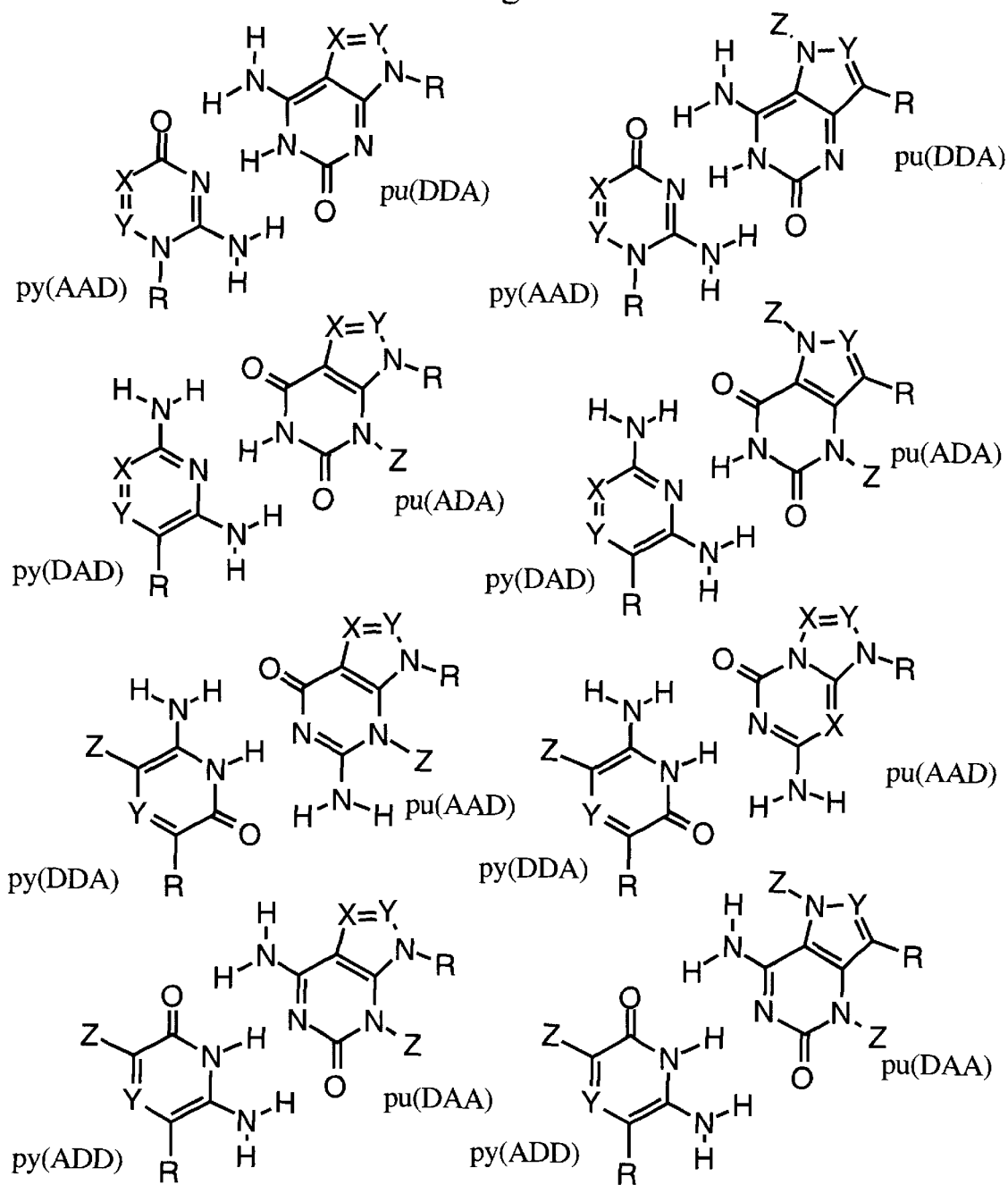
FIG. 4: Generalized structures for 4 non-standard base pairs formed between 8 non-standard bases
Figure 6:
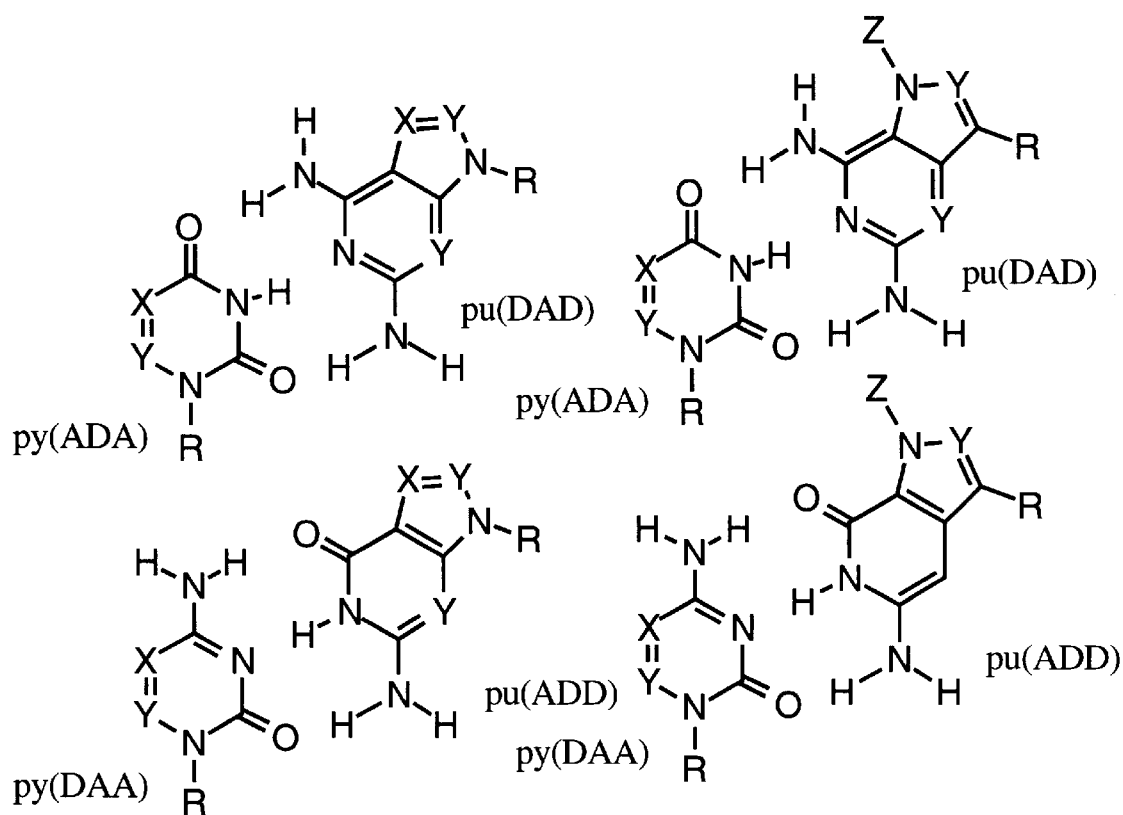
FIG. 6: Generalized structures for 2 standard base pairs formed between the 4 standard bases
Figure 7:
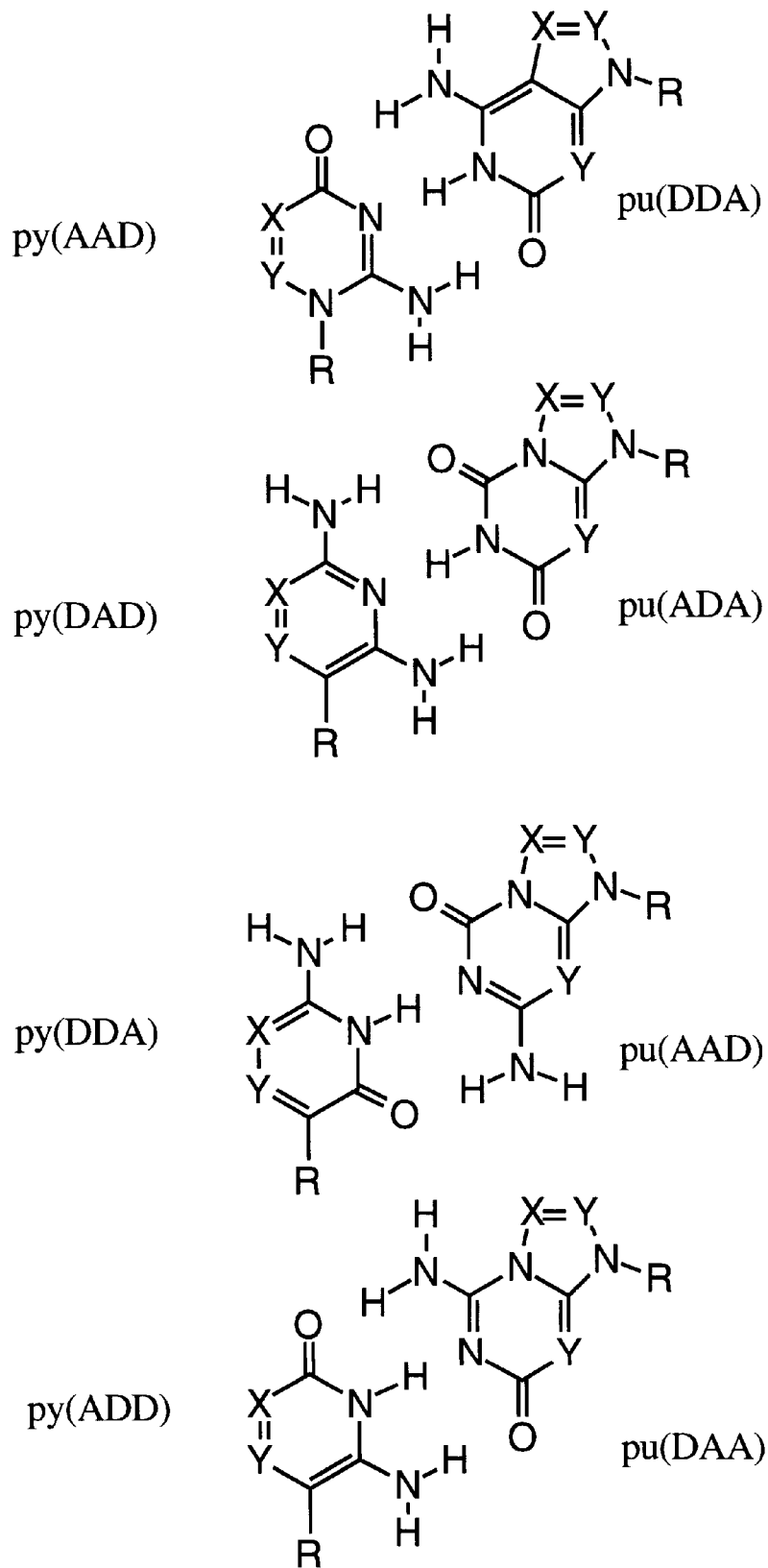
FIG. 7: Additional implementations of the non-standard hydrogen bonding patterns.

Much work was directed towards the pyridine nucleoside analog, 3-β-D-ribofuranosyl-(2,6-diamininopyridine). However, the presently preferred base pairs are those where the six-ring pyrimidine analog is joined to a ribose or deoxyribose ring via a carbon-carbon bond, and where the pyrimidine analog contains at least two nitrogens in the ring itself. Given an appropriate arrangements of hydrogen bond donating and accepting groups, many ring systems are appropriate (FIG. 4), including ring systems to which are appended functionalized and unfunctionalized side chains. Syntheses for many of these compounds are known in the prior art. However, there are several constraints on the ring system and its substituents. First, the ring systems must be aromatic so that they are capable of stacking with bases above and below in the double helix. Second, substituent on the 6 position of the pyrimidine (or the analogous position of a pyrimidine analog) and the 8 position of the purine (or the analogous position of a purine analog) is preferably no larger than hydrogen.

The most preferred pyrimidine analog is 3-β-D-ribofuranosyl-(2,6-diaminopyrimidine), trivially designated here as K. Several complementary purines are presently preferred. For example, either xanthosine or 3-β-D-ribofuranosyl-(1-methyl-pyrazolo[4,3-d]pyrimidine-5,7 (4H,6H)-dione), also known as 7-methyl oxoformycin B, have been found to form base pairs with K when incorporated into DNA and RNA.

Since Ser. No. 07/594,290, now U.S. Pat. No. 5,432,272, was filed, continued experimental work has increased the number of embodiments of the method claimed, and the compositions of matter that can be prepared using the method. An even wider range of polymerases has been shown to incorporate non-standard base pairs into duplex oligonucleotides, including the reverse transcriptase from human immunodeficiency virus 1, especially this polymerase with the smaller subunit removed, and the thermostable polymerases from *Thermotoga maritima, Pyrodictium abyssi,* and *Pyrodictium occultum.* The py(ADD) base in its pyrazine form has been incorporated into an oligonucleotide using T4 RNA ligase (J. J. Vögel and S. A. Benner. *J. Am. Chem. Soc.* 116, 6929–6930 (1994)), which is incorporated herein by reference.

Further, since Ser. No. 07/594,290, now U.S. Pat. No. 5,432,272, was filed, continued experimental work has increased the number of routes available for the preparation of non-standard bases as components of oligonucleotides. J. J. Vögel, M. M. Altorfer, S. A. Benner. *Helv. Chim Acta* 76, 2061–2069 (1993); U. von Krosigk, *Entwurf und Synthese eines Neuen Basenpaars,* Diss. ETH Nr. 10164, 1993; J. V ögel, *Warum verwendet die Natur nur zwei Basenpaare für das genetische Alphabet? Ein Fragment einer Antwort,* Diss. ETH Nr. 10691, 1994).

Figure 8:
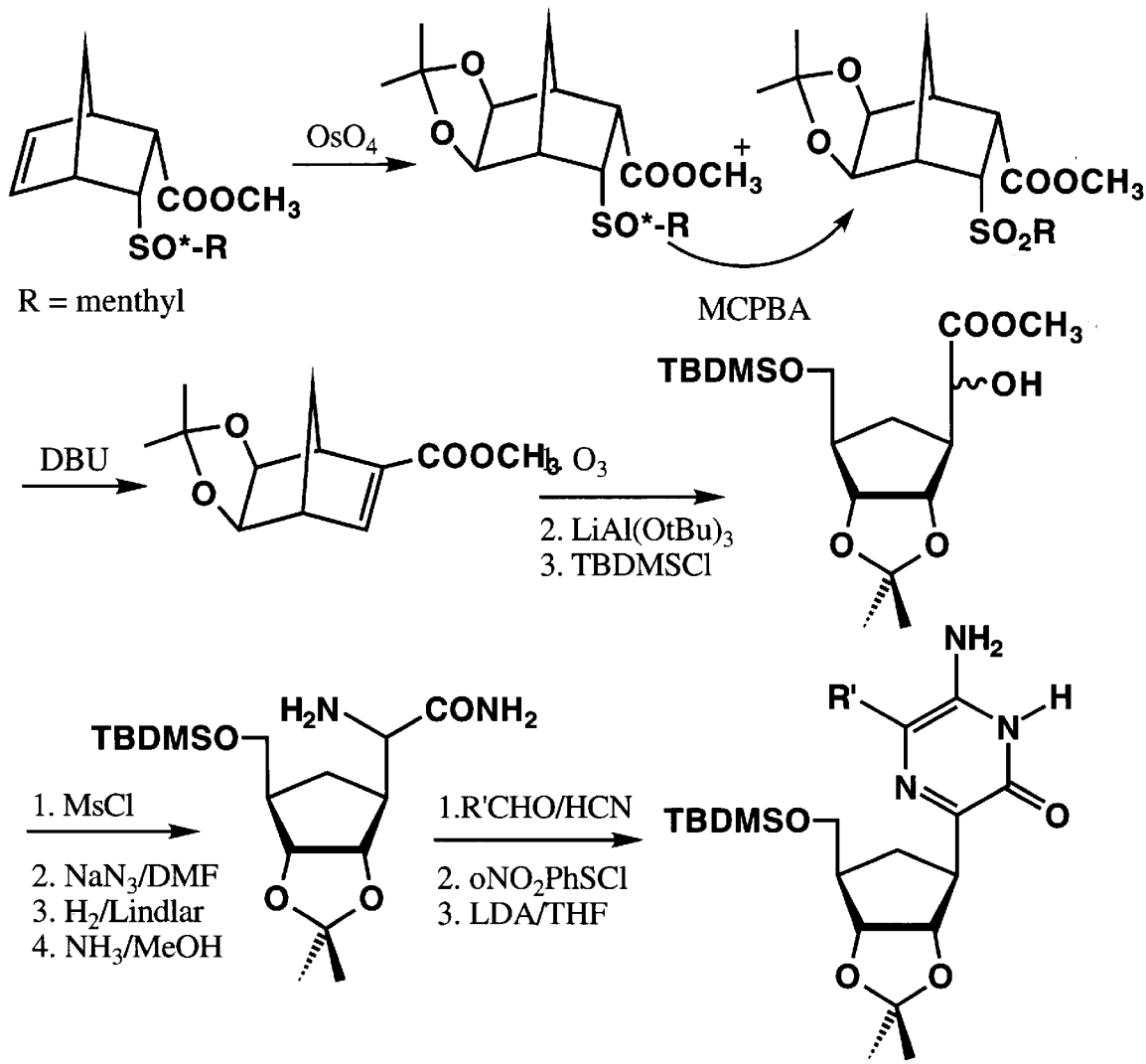
FIG. 8. Synthesis of a carbocyclic version of the py(DDA) nucleoside analog.

Additional information has been gathered concerning the properties of the non-standard heterocyclic systems. J. J. V ögel, U. von Krosigk and S. A. Benner. *J. Org. Chem.* 58, 7542–7547 (1993), and further heterocyclic ring systems have bee defined that implement the non-standard hydrogen bonding patterns disclosed in U.S. Pat. No. 5,432,272. Further, functional groups Z have been found to be preferred when the attachment to carbon is via an acetylenic linkage, as disclosed in Hobbs, Jr., F. W. (1989) (*J. Org. Chem.* 54, 3420–3422).The py(DDA) and py(ADD) implementations have been found to be most preferably implemented on carbocyclic analogs of ribose and deoxyribose rings (FIG. 8).

Finally, additional information has been collected to demonstrate the utility of compositions of matter that are oligonucleotides containing non-standard bases. J. D. Bain, A. R. Chamberlin, C. Y. Switzer and S. A. Benner. *Nature* 356, 537–539 (1992). These oligonucleotide analogs also have utility as mixtures of random sequences, where the mixture (or library) is presented to a preselected receptor, usually immobilized on a solid support. Preferably the oligonucleotide analogs are from 6 to 300 nucleotides in length. Preferentially, the receptor is a protein that is an interesting biological target (e.g. thrombin) that is affixed to an agarose or Sepharose support. Those oligonucleotide analogs that have affinity for the receptor bind to the receptor; those analogs that do not have affinity are washes from the receptor. This is referred to as a "separation" step, and is well known in the art.

In the next step, oligonucleotide analogs that bind by to the receptor are eluted from the receptor, preferably by increasing the concentration of salt in the medium, by adjusting the pH, or by adding ligands. These oligonucleotide analogs, which have affinity for the receptor, are the amplified by the template-directed polymerization method disclosed in U.S. Pat. No. 5,432,272 , by using either a DNA polymerase or an RNA polymerase. This yields larger amounts of a mixture of oligonucleotide analogs enriched in analogs that have affinity for the receptor. Structural variation in the amplified products is then created by "error prone" copying using methods disclosed in U.S. Pat. No. 5,432,272 and related methods well known in the art.

By repeating the cycle of separation, amplification, and variation from 2 to 20 additional times, the population of oligonucleotide analogs is said to "evolve" to include increasingly higher fractions of oligonucleotide analogs with increasingly higher affinties for the preselected receptor. Thus, the method and compositions disclosed in U.S. Pat. No. 5,432,272 have additional utility in methods for generating ligands for receptors.

EXAMPLE 1

The K-P Base Pair

The pyrimidine 3-β-D-ribofuranosyl-(2,6-diaminopyrimidine), trivially designated as K, presents a donor-acceptor-donor hydrogen bonding pattern to a complementary strand in a duplex structure. K as a deoxyriboside derivative suitable for automated DNA synthesis was synthesized from a known precursor by routes known in the prior art. C. K. Chu, U. Reichman, K. A. Watanabe, J. J. Fox, *J. Org. Chem.* 1977, 42, 711. Two purine analogs were chosen to complement K. The first, xanthosine (X), is a natural base available commercially as both the nucleoside and nucleoside triphosphate. However, because of concerns that deoxyxanthosine might undergo depurination in some of the studies planned, another complementary base, 3-β-D-ribofuranosyl-(1-methyl-pyrazolo[4,3-d]pyrimidine-5,7 (4H,6H)-dione) (B. G. Ugarkar, G. R. Revankar, R. K. Robins, *J. Heterocycl. Chem.*, 21, 1865–1870 (1984)), also known as 7-methyl oxoformycin B, and trivially designated here as P, was prepared by routes known in the prior art. In P, the heterocyclic base is joined to the pentose ring by a carbon-carbon bond.

The K-P base pair has physical and chemical properties suitable as replicatable components of a genetic alphabet (J. A. Piccirilli, T. Krauch, S. E. Moroney, S. A. Benner, *Nature*, 343, 33–37 (1990). In a solution of a derivative of K in chloroform, a strong nuclear Overhauser enhancement (NOE) between the proton at C1' of the ribose ring and the proton at C4 of the heterocyclic ring suggested that K adopts the undesired syn conformation when alone in solution. However upon addition of a protected derivative of the complementary purine nucleoside P, this NOE largely disappeared. Further, when both K and its complement are present, the resonances assigned to the amine protons of K shift strongly downfield, as does the resonance of P assigned to the nitrogen flanked by the carbonyl groups. These facts together show that K and P form a standard Watson-Crick base pair in a solution of chloroform.

To determine the effect of a base pair between K and P on the stability of a DNA duplex, several oligonucleotides containing the K-P base pair were synthesized using an Applied Biosystems Oligonucleotide Synthesizer. Melting studies showed that duplexes containing a K-P base pair are only slightly less stable than duplexes containing only natural bases. Further, duplexes containing the new base pair are considerably more stable than those containing mismatches involving the new bases, which in turn had melting temperatures similar to duplexes containing mismatches of natural bases (Piccirilli et al., op. cit.). The stability of various mismatches was consistent with the presumed stability of "wobble" base pairs, which should be particularly important for the GT and AK mismatches. These results suggested that enzymatic incorporation of a new base selectively opposite its complement in a DNA template should be possible, provided that natural DNA and RNA polymerases accepted the new bases.

To demonstrate that xanthosine triphosphate could be incorporated enzymatically into an RNA oligonucleotide opposite a K in the template to yield the compositions claimed here, a promoter-template including a promoter sequence for T7 RNA polymerase (Milligan, J. F., Groebe, D. R., Witherell, G. W., & Uhlenbeck, O. C. *Nucleic Acids Res.*, 15, 8783 (1987), (17 bases) followed by a short oligonucleotide segment (7 bases), the new base K, 1 additional base, and a final A was synthesized, together with a complementary 18 base primer (FIG. 5). Incorporation of K into the synthetic DNA templates was verified by digestion of samples of the template with snake venom phosphodiesterase, hydrolysis of the phosphate from the products with bacterial alkaline phosphatase, and analysis of the resulting nucleosides by HPLC (data not shown). Control templates containing T replacing K were also prepared by synthesis. Transcription of the primed templates could be detected most simply by the incorporation of radiolabled UMP (from a-labeled UTP) into a product RNA molecule 10 bases long (the "full length product").

When synthetic template 1 was incubated with labeled UTP and various other nucleoside triphosphates, full length products were observed in the presence of XTP. The efficiency of synthesis of full length product from templates with and without K was approximately the same, provided that the necessary complementary nucleoside triphosphates were all present in the incubation mixtures. In absence of XTP, a significant amount of full length product could be detected only in the presence of ATP, and this at somewhat low levels (ca. 24%, measured by scintillation counting of bands cut from the gel). Such a misincorporation presumably occurs via "wobble" base pairing, and is not infrequent even with natural bases when incorporation experiments are run in incubation mixtures that are missing one component. Coleman, J. E., Martin, C. T. & Muller, D. K. *Biochemistry*, 27, 3966 (1988)

To determine whether misincorporation of A was diminished by competition with X, experiments were performed with tritiated XTP (synthesized from tritiated GTP by Demijanov oxidation) Roy, K. B. & Miles, H. T. *Nucleosides and Nucleotides*, 2, 237 (1983) and $\gamma$-$^{32}$P-labeled GTP (which is incorporated, with the triphosphate intact, at the 5') end of the RNA product) together in an incubation mixture in varying ratios. Full length products from an incubation containing a 1:1 molar ratio of $^3$H-XTP and unlabeled ATP were isolated by gel electrophoresis, the bands excised, and the relative amounts of $^3$H and $^{32}$P determined by scintillation counting. After correction for the specific activities of the starting nucleotides, the misincorporation of adenosine into the product at a XTP:ATP ratio of 1:1 was reduced to ca. 14%. Infidelity further decreases with increasing ratios of X:A, and most likely stems from errors made by the polymerase itself rather than from minor tautomers of the bases.

To demonstrate that xanthosine triphosphate could be incorporated into a DNA oligonucleotide opposite a K in the template, a set of primer-templates (FIG. 5) were prepared containing either K, C or T (the latter two serving as control templates). Incorporation of K into the synthetic DNA templates was again verified by digestion of samples of the template with snake venom phosphodiesterase, removal of the phosphate from the products by bacterial alkaline phosphatase, and analysis of the resulting nucleosides by HPLC. As before, the last base in the template was a unique A, permitting the detection of full length products most simply by autoradiography following the incorporation of $\alpha$-$^{32}$PTTP.

The synthetic primer-templates were incubated with the Klenow fragment of DNA polymerase I (Pol 1) Cobianchi, F. & Wilson, S. H. *Meth. Enzymol.*, 152, 94 (1987) in the presence of various nucleoside triphosphates, and the products analyzed by gel electrophoresis. K in the template directed the incorporation of XTP into full length product. Upon electrophoresis, the product containing X migrates faster than the analogous products containing G or A, presumably because the xanthine heterocycle carries an additional negative charge under the conditions of the electrophoresis due to its low $pK_a$ ($pK_a$=5.7). Direct evidence for the incorporation of xanthosine was obtained by digestion of the product oligonucleotide, kinasing, and electrophoretic analysis.

To measure the relative efficiency as templates of the oligonucleotides containing different bases, product bands from electrophoresis gels were excised and their radioactivity determined by liquid scintillation counting. Templates containing K were ca. 70% as efficient at directing the synthesis of full length product (in the presence of XTP) as those containing only natural bases.

The fidelity of incorporation of X opposite K was examined by incubating templates containing C, T and K with purine triphosphates separately and in competition (FIG. 5). As expected, the fidelity of incorporation was considerably higher with DNA polymerase than with T7 RNA polymerase. Essentially no G or A was incorporated by the Klenow fragment of DNA polymerase opposite K, and essentially no X was incorporated opposite T in the template. The only evidence of infidelity was a low level (ca. 5%) of X misincorporated opposite C in the template when GTP was missing from the incubation mixture. This misincorporation was not observed at all when GTP and XTP were present in a 1:1 ratio.

EXAMPLE 2

The isoC-iso-G Base Pair

Protected d-iso-C suitable as a building block for the chemical synthesis of DNA was synthesized by direct extensions of standard methods. Watanabe, K. A.; Reichman, C. K.; Fox, J. J. *Nucleic Acid Chemistry*; Tipson, R. S.; Townsend, L. B., Eds.; John Wiley and Sons: New York 1978; Part 1, p 273. (b) Kimura, J.; Yagi, K.; Suzuki, H.; Mitsunobu, O. *Bull. Soc. Chem. Jap. 1980, 53, 3670.* $N^2$-benzoyl-5'-dimethoxytrityl-d-iso-C diisopropyl phosphoramidite, used directly in machine-DNA synthesis, was synthesisized from d-iso-C by the general procedure of Atkinson and Smith: Atkinson, T.; Smith, M. *Oligonucleotide Synthesis: A Practical Approach*; Gait, M. J. Ed.; IRL Press: Oxford 1985; pp 35–82. This was incorporated into two templates, and three other templates containing only natural bases were synthesized for use as standards and controls. An 8-mer primer was annealed to the appropriate templates (FIG. 5) to provide a double stranded binding site for the Klenow fragment of DNA polymerase I (*E. coli*), followed by a single stranded coding region containing d-iso-C flanked only by purine nucleotides. Alternatively, different templates (FIG. 5) were annealed to an 18-mer to give the double stranded promoter region required by T7 RNA polymerase, followed by a single stranded coding region containing d-iso-C. In all of the templates, a unique A at the end of the coding strand was included to direct the incorporation of radiolabelled T or U and ribo- and deoxyribo-iso-GTP's. Mantsch, H. H. et. al., *Biochemistry* 1975, 14, 5593. The reactions with the Klenow fragment were conducted by incubating template/primer, polymerase, and a mixture of the required dNTPs including ($\alpha$-$^{32}$P)TTP. Following incubation, the products were analyzed by gel electrophoresis and autoradiography. With primed templates containing iso-C, full length product was obtained only with d-iso-GTP present in the incubation mixture. The presence of iso-G at the correct position in the product oligonucleotide was positively established by a "nearest neighbor" analysis, Sgaramella, V.; Khorana, H. G. *J. Mol Biol.* 1972, 72, 427. and by the "minus" sequencing method. Sanger, F.; Coulson, A. R. *J. Mol Biol.* 1975, 94, 441. As expected, in an incubation of a primed template containing T with dATP and the required dNTPs in the absence of d-iso-GTP, full length product was observed only to the extent anticipated by the fact that a small amount (15%) of dUTP was present in the template due to the deamination of iso-C (vide supra).

Infidelity between iso-G and T was anticipated due to the known existence of a minor "phenolic" tautomer of iso-G in addition to the major $N_1$-H tautomer (Sepiol, J., Kazimierczuk, Z., Shugar, D. Z. *Naturforsch.*, 1976, 31c, 361; the possibility that this minor tautomer could form a Watson-Crick base pair with T was recognized on theoretical grounds. In fact, incubation of a primed template containing T in place of d-iso-C with the required dNTPs and d-iso-GTP did yield a significant amount of full length product. This result strongly suggests that polymerases synthesize a base pair between T and the "phenolic" tautomer of iso-G. This fact diminishes the value of the base pair between iso-G and iso-C for many (but not all) applications.

In analogous experiments, T7 RNA polymerase was shown to accept the new base pair. Incubation of a template (FIG. 5) possessing the T7 promoter with the required NTPs yielded more full length product in the presence iso-GTP than in its absence. Sequencing of the RNA transcript positively established the presence of iso-G in the product at the expected position.

EXAMPLE 3

Oligonucleotides containing the py(ADD) base

Figure 9:
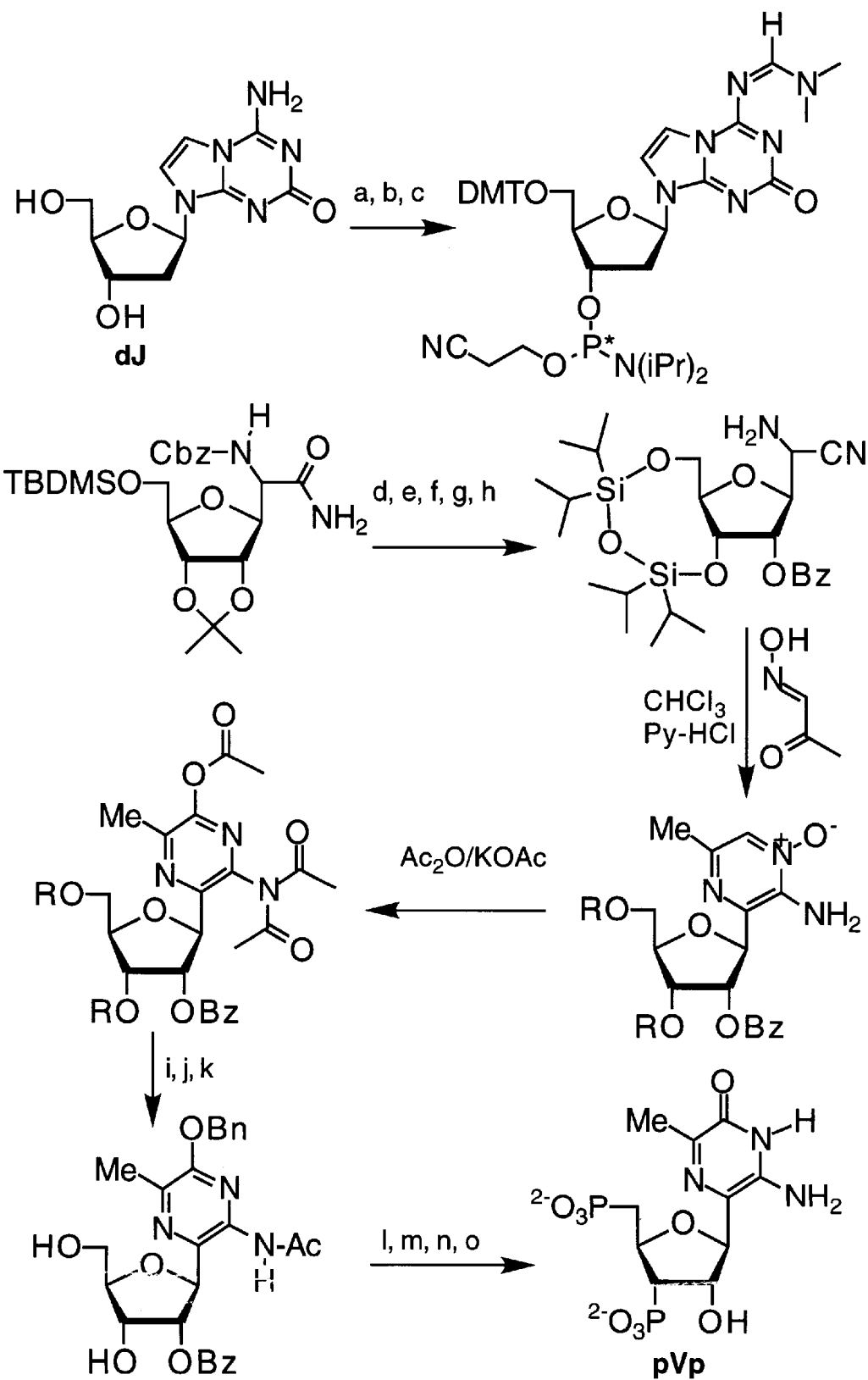
FIG. 9. Synthesis of an oligonucleotide containing the py(ADD) non-standard base.

The 2'-deoxyriboside of the donor-acceptor-acceptor purine analog (Voegel, J. J.; Altorfer, M. M.; Benner, S. A. *Helv. Chim. Acta* 1993, 76, 2061–2069) was protected and converted into a phosphoramidite suitable for incorporation into a DNA strand by automated synthesis (FIG. 9). The oligonucleotides were synthesized on a "Gene Assembler Plus" of Pharmacia. Except for the coupling step involving dJ, where the reaction time was doubled from 1.5 to 3.0 min., the standard parameters were used. Due to the instability of dJ in conc. $NH_3$ (aq) at elevated temperatures, "PAC-amidites" of the natural bases were used; these were deprotected under milder conditions ($NH_3$aq/EtOH=3:1, 3h at room temperature followed by 1 h at 55° C. The riboside 3',5'-bisphosphate (pVp) of the acceptor-donor-donor pyrimidine analog was prepared from a known precursor[3] (FIG. 2). An oligoribonucleotide containing V was built by sequential addition of pVp and pAp to a starting oligoribonucleotide (A RP-C18-HPLC purified O-2'-Fpmp- and O-5'-DMT-protected 4-mer was purchased from MWG-Biotech, deprotected according to the manufacturers instructions, and isolated by RP-C18-HPLC.) using T4 RNA ligase and alkaline phosphatase following the procedure of Uhlenbeck and coworkers and Middleton et al. (England, T. E.; Uhlenbeck, O. C. *Biochemistry* 1978, 17, 2069. Barrio, J. R.; Barrio, M. G.; Leonard, N. J.; England, T. E.; Uhlenbeck, O. C. *Biochemistry* 1978, 17, 2077. Romaniuk, P. J.; Uhlenbeck, O. C. *Methods Enzymol.* 1983, 100, 52. Middleton, T.; Herlihy, W. C.; Schimmel, P. R.; Munro, H. N. *Anal. Biochem.* 1985, 144, 110) (FIG. 9). All oligonucleotides were purified by HPLC. Both the incorporation of dJ and V into the oligonucleotides and the relative nucleoside composition were verified by digestion of oligonucleotide samples and HPLC analysis of the resulting nucleoside mixtures (Seela, F.; Lampe, S. Helv. Chim. Acta 1991, 74, 1790–1800). The identity of the peak assigned to the unnatural nucleosides was proven by coinjection with synthetic dJ and V. After each coupling cycle, the products were purified by HPLC to yield product containing V only in the beta configuration. The V present in the fmal oligonucleotide was >90% in the beta configuration. FIG. 9 shows a schematic diagram of the various syntheses, with the following key: a) DMF-diethylacetal, DMF; b) DMTCl, pyridine, DMF; c) ClP(N(iPr)$_2$)OCH$_2$CH$_2$CN, Hünigs base, CH$_2$Cl$_2$; d) TFA/H$_2$O =4/1; e) TFAA/pyridine/dioxane; f) TipsCl, imidazole, DMF; g) BzCl, pyridine; h) Pd-C/H$_2$/MeOH; i) EtOH, rf.; j) PhCH$_2$OH, DEAD, Ph$_3$P, THF; k) pyridine-HF, pyridine, 0° C.; l)(BnO)$_2$PN(iPr)$_2$, tetrazole, CH$_3$CN, DMF; m) N-methyl-morpholine-N-oxide, CH$_3$CN, DMF; n) Pd-C/H$_2$, THF, Et$_3$NHCO$_3$ aq; o) H$_2$NNH$_2$×H$_2$O; p) T4 RNA q) alkaline phosphatase.

What is claimed is:

1. An oligonucleotide analog in which one or more of the constituent nucleotide units has the formula

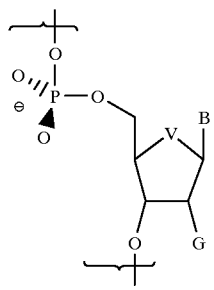

wherein

G is selected from the group consisting of —H and —OH,

V is —O—, and B is a nucleobase analog independently selected from the group consisting of

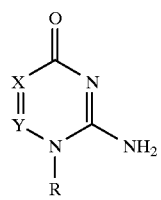 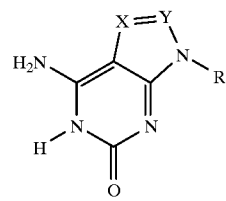

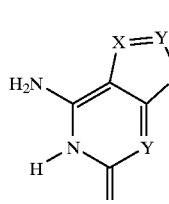 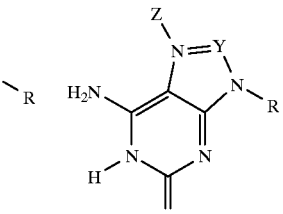

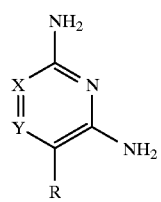 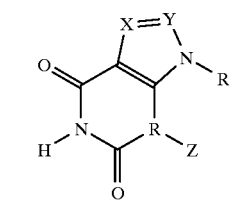

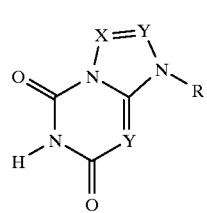 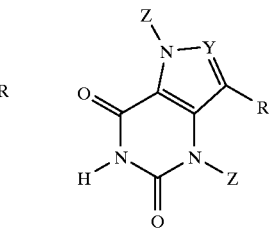

-continued

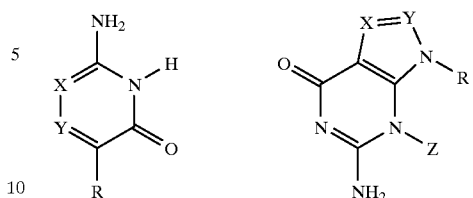

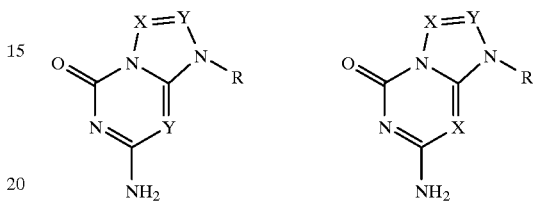

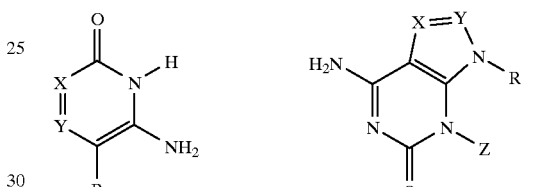

wherein

—R designates the point of attachment of the heterocycle to the oligonucleotide analog, X is selected from the group consisting of a nitrogen atom and a carbon atom bearing a substituent Z, Z is a moiety selected from the group consisting of hydrogen and —CH₃, Y is selected from the group consisting of N and CH, said ring structure of said nucleobase analog comprises no more than three nitrogen atoms consecutively bonded, and wherein the oligonucleotide analog is not a homopolymer of iso-guanine.

2. The oligonucleotide analog of claim 1, wherein said nucleobase analog is selected from the group consisting of

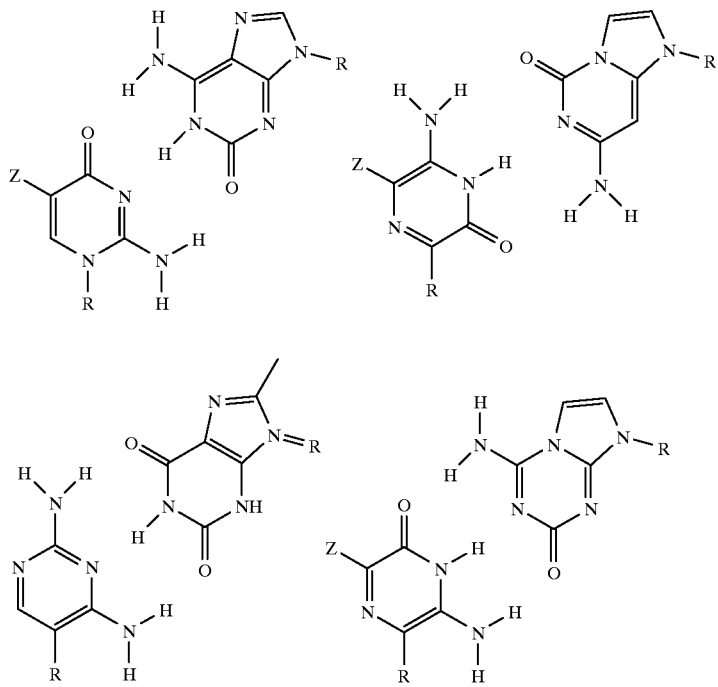

wherein Z is selected from the group consisting of H— and CH₃, and wherein —R designates the point of attachment of the heterocycle to the oligonucleotide analog.

3. A method for obtaining an oligonucleotide analog that has a target binding property to a pre-selected receptor, said method comprising:

preparing a mixture of oligonucleotide analogs of random sequences;

contacting said analogs with said receptor under conditions wherein said analog that binds to said receptor can be separated from said mixture as a binding analog; and separating said binding analog from non-binding analogs, wherein one or more of the constituent nucleotide units of said oligonucleotide analog has the formula

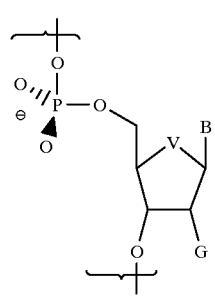

wherein

G is selected from the group consisting of —H and —OH,

V is —O—,

B is a nucleobase analog comprising a ring structure, selected from the group consisting of

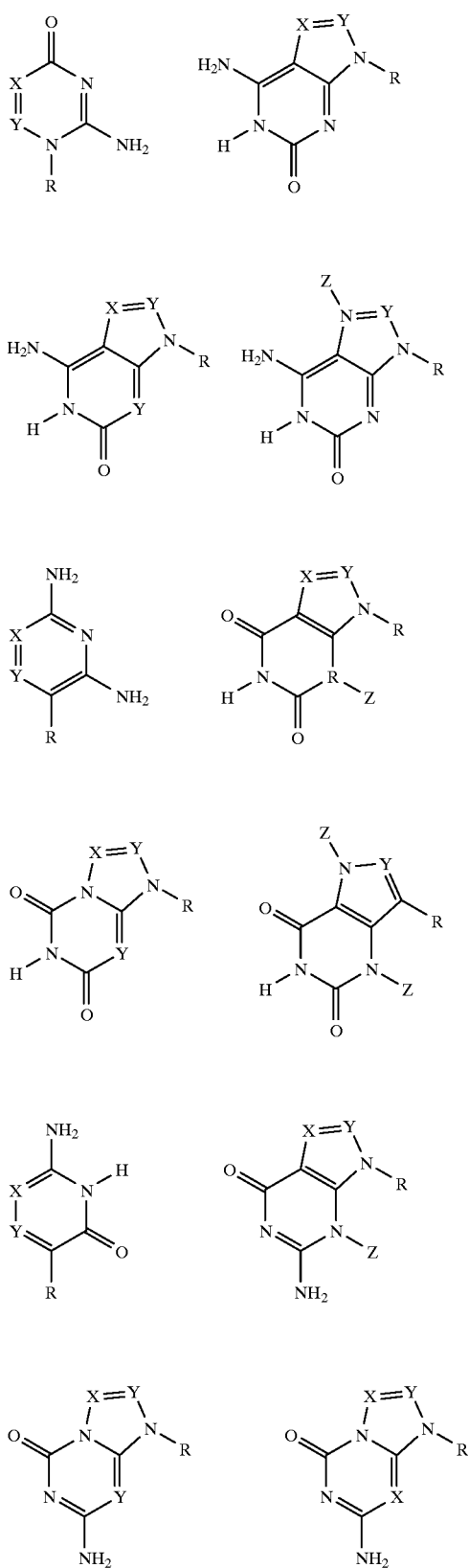
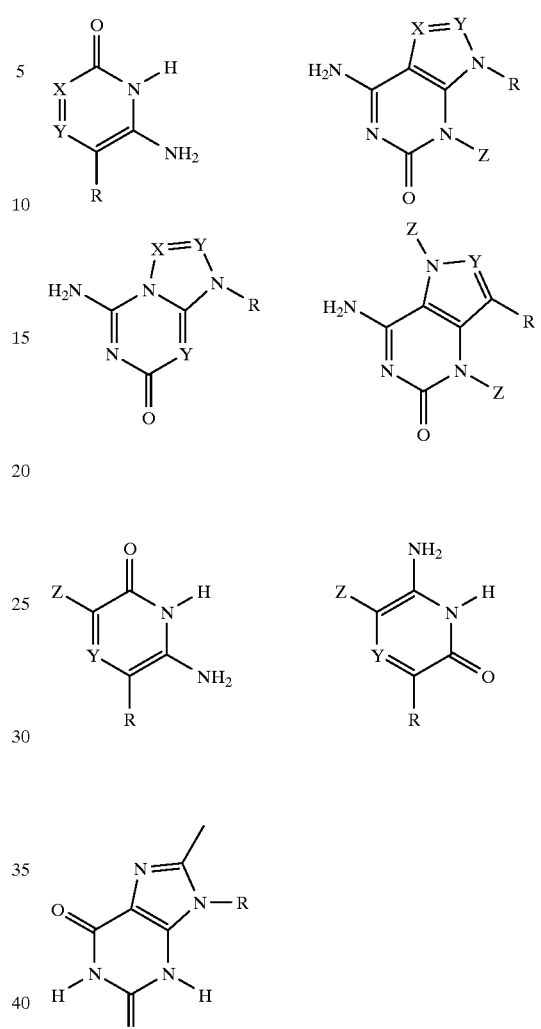

wherein
—R designates the point of attachment of the heterocycle to the oligonucleotide analog,
X is selected from the group consisting of a nitrogen atom and a carbon atom bearing a substituent Z,
Z is a moiety selected from the group consisting of hydrogen and —CH$_3$,
Y is selected from the group consisting of N or CH, and
said ring structure of said nucleobase analog comprises no more than three nitrogen atoms consecutively bonded.

4. The method of claim 3, further comprising:
generating a mixture of mutated and non-mutated oligonucleotide analogs from said binding analog; and
repeating said contacting and separating steps.

5. The method of claim 4, further comprising:
said generating, contacting, and separating steps are repeated from 2 to 20 times.

6. The analog of claim 1, wherein said oligonucleotide analog has between 6 and 300 nucleotide units.

* * * * *

```
                           SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 13
         (B) TYPE: nucleic acid
         (C) STRANDEDNESS: single
         (D) TOPOLOGY: linear (xi) SEQUENCE DESCRIPTION: SEQ ID NO:1:

AGTGGTCAAA ATC                                                          13

(2) INFORMATION FOR SEQ ID NO:2:

(i) SEQUENCE CHARACTERISTICS:
         (A) LENGTH: 13
         (B) TYPE: nucleic acid
         (C) STRANDEDNESS: single
         (D) TOPOLOGY: linear (xi) SEQUENCE DESCRIPTION: SEQ ID NO:2:

AGCGGTCAAA ATC                                                          13

(2) INFORMATION FOR SEQ ID NO:3:

(i) SEQUENCE CHARACTERISTICS:
         (A) LENGTH: 18
         (B) TYPE: nucleic acid
         (C) STRANDEDNESS: single
         (D) TOPOLOGY: linear (xi) SEQUENCE DESCRIPTION: SEQ ID NO:3:

TAATACGACT CACTATAG                                                     18

(2) INFORMATION FOR SEQ ID NO:4:

(i) SEQUENCE CHARACTERISTICS:
         (A) LENGTH: 27
         (B) TYPE: nucleic acid
         (C) STRANDEDNESS: single
         (D) TOPOLOGY: linear (xi) SEQUENCE DESCRIPTION: SEQ ID NO:4:

AGCCCGGCGC TATAGTGAGT CGTATTA                                           27
```